United States Patent
Healy et al.

[11] Patent Number: 5,972,291
[45] Date of Patent: *Oct. 26, 1999

[54] METHOD AND APPARATUS FOR DISPOSAL OF INFECTIOUS AND MEDICAL WASTE

[75] Inventors: Thomas Healy, Brookfield, Conn.; Eric Schink, Wappenger Falls, N.Y.; Jonathan Bricken, Ridgefield, Conn.

[73] Assignee: Thermal Waste Technologies, Inc., Bethel, Conn.

[*] Notice: This patent issued on a continued prosecution application filed under 37 CFR 1.53(d), and is subject to the twenty year patent term provisions of 35 U.S.C. 154(a)(2).

[21] Appl. No.: 08/794,214

[22] Filed: Jan. 30, 1997

[51] Int. Cl.⁶ ............................................. A61L 2/00
[52] U.S. Cl. ..................... 422/22; 422/122; 422/307; 422/308; 422/900; 588/900
[58] Field of Search ................... 422/122, 307, 422/308, 900, 22; 588/900

[56] References Cited

U.S. PATENT DOCUMENTS

| | | | |
|---|---|---|---|
| 4,992,217 | 2/1991 | Spinello | 264/0.5 |
| 5,078,924 | 1/1992 | Spinello | 264/0.5 |
| 5,124,125 | 6/1992 | Brent | 422/21 |
| 5,185,126 | 2/1993 | Adamski et al. | 422/38 |
| 5,213,758 | 5/1993 | Kawashima et al. | 422/21 |
| 5,223,231 | 6/1993 | Drake | 422/297 |
| 5,230,292 | 7/1993 | Workman et al. | 110/210 |
| 5,240,656 | 8/1993 | Scheeres | 264/37 |
| 5,248,486 | 9/1993 | Matsuoka et al. | 422/294 |
| 5,256,861 | 10/1993 | Anthony | 219/494 |
| 5,270,000 | 12/1993 | Goldner et al. | 422/21 |
| 5,277,869 | 1/1994 | Glazer et al. | 422/26 |
| 5,282,428 | 2/1994 | Greville et al. | 110/250 |
| 5,348,704 | 9/1994 | Tanaka | 422/22 |
| 5,364,602 | 11/1994 | Leduc | 422/307 |
| 5,370,066 | 12/1994 | Workman et al. | 110/346 |
| 5,401,444 | 3/1995 | Spinello | 264/0.5 |
| 5,422,074 | 6/1995 | Scimidt | 422/28 |
| 5,476,634 | 12/1995 | Bridges et al. | 422/22 |
| 5,523,052 | 6/1996 | Bridges et al. | 422/22 |

FOREIGN PATENT DOCUMENTS

| | | |
|---|---|---|
| 8003576 | 5/1980 | Sweden . |
| WO93/06418 | 1/1993 | WIPO . |
| WO95/21633 | 8/1995 | WIPO . |

*Primary Examiner*—Krisanne Thornton
*Attorney, Agent, or Firm*—Mintz, Levin, Cohn, Ferris Glovsky and Popeo, P.C.

[57] ABSTRACT

An apparatus and method for rendering infectious and medical waste safe through heating and the disposal of said waste includes a body portion with a chamber to receive a container of medical waste. The chamber is connected with a filter for biological materials which escape from the waste container during heating. The contaminants are directed toward the filter by flowing out gas from the container in a predetermined direction as the waste container is heated to a temperature of preferably not less than 350° F. and preferably not more than 385° F. to render the waste biologically safe and unreusable.

26 Claims, 8 Drawing Sheets

METHOD AND APPARATUS FOR DISPOSAL OF INFECTIOUS AND MEDICAL WASTE

FIELD OF THE INVENTION

This invention relates to an apparatus and method for disposal of infectious and medical waste, and more particularly to rendering medical and infectious waste safe and sterile utilizing a thermal process.

BACKGROUND OF THE INVENTION

The safe handling and disposal of regulated medical waste from various medical and health care facilities is a well-known problem. Of particular concern is the safe processing of contaminated needles, scalpels, and sharp metal or glass objects which have come into contact with the human body or bodily fluids. These items often include thermoplastic materials such as those found in syringes and tubing, vials of glass and other objects which have contacted bodily fluids.

Numerous environmental regulations have been enacted which prevent the use of conventional methods of waste disposal. On-site methods to render the infectious and medical waste safe have not proven to be practical or cost-efficient. Although the prior art discloses numerous examples of sterilization through the use of electronic beam radiation, gamma rays, heat, and even microwave energy, numerous problems still exist.

Sterilization by autoclaving, for example, does not solve the potential problems since sterilization is labor intensive and subject to human error. This sterilization method also does not change the dangerous nature of "sharps" materials such as needles and scalpels, and further does not render syringe tubes and parts unrecognizable or unusable.

The problems associated with used thermoplastic hypodermic needles and syringes are well known. These contaminated and dangerous handling materials resist decay and are often sought by illegal drug users. Past disposal techniques involve the requirement of medical facilities to cut the needle from the syringe body immediately after injection. This procedure, however, was discovered to spread disease through airborne aerosols caused by the mechanical sheering action. The contaminated needle tip and syringe would then still need to be handled and disposed of as a regulated waste item. More recent developments have lead to depositing the syringe and needle into a "sharps" container. The sharps container would then be delivered to an authorized facility in a costly "tracking" process.

A prior art device is capable of destroying the needle at the point of use through low voltage electric current. The needle is reduced along with all associated contaminants, at temperatures of incandescence by passing the current through the needle. This process leaves a sterile and incinerated residue, but suffers the drawback of not having the capability to render safe other commonly used materials, such as scalpels, glass, or leftover syringe parts. Other prior techniques handle sharp items by encasing the needles and scalpels in gels, resins, or thermoplastics. U.S. Pat. No. 4,662,516 to Baker Sr. et al., discloses such a technique. In Baker, et al., a thermoplastic bag with waste is melted at an autoclave temperature and is capable of encapsulating the medical waste. The product of this system, however, remains a hazardous material for handling purposes. The treated waste is recognizable and can be unsterile. The needles project from the solid mass, making them exposed and extremely dangerous. Further, autoclave sterilization depends on "wet heat" destroying microbial life by having the heat contact the life forms for a defined period of time. The autoclave sterilization process is not efficient when the waste is shielded by plastic bags or immersed in a liquefied or melted plastic.

An additional problem which these devices have not addressed, is the fact that infectious and hazardous fumes are discharged from the waste material as it is heated. These fumes contain chemicals from the thermoplastic syringes, various medications, body fluids, and other chemicals in addition to biological contaminants. U.S. Pat. No. 5,240,656 issued to Scheeres discloses a method and apparatus for treating contaminated plastic waste and discloses the use of a carbon filter for the purpose of removing any odors. The Scheeres system, however, does not handle the problem of filtering biological and viral contaminants within the fumes and does not disclose a method of directing air towards the filter.

The heating of several different waste materials at one time also creates the problem of non-uniform heating throughout the container. This leads to unpredictability with gas discharge. Several of the prior methods are also not capable of handling all types of medical waste. That is, many of the prior art systems are capable of handling syringes, but not capable of handling soft wastes such as gauze, tape and fabrics for sterilization purposes in a single on-site system.

SUMMARY OF THE PRESENT INVENTION

The present invention provides an apparatus and method for heat treating medical waste with an on-site medical waste processing system. The system is capable of processing all types of infectious medical waste with the exception of human and animal body parts, radioactive waste and chemotherapeutic waste. The medical waste is preferably heated to a predetermined temperature of not less than 350° F. and not more than 385° F. to melt all the plastic portions of the waste, render the sharps material and soft/red bag waste sterile and either unrecognizable or unreusable. Furthermore, this single on-site system assures that essentially all out gas from the heat waste container flows in a predetermined path which allows the operating environment outside the system to remain free of airborne biological and chemical contaminants. This is done by means of a filter, preferably an antiviral/antibacterial and odor trapping filter, which is placed between the processing container and the exhaust. Finally, the problem of inconsistent and unpredictable gas discharge from the uneven heating of undetermined waste compositions is solved by a reservoir to provide an additional safety volume of space for gas expansion within the chamber where the canister is placed.

The apparatus for thermal processing of medical waste includes a body portion with an inner housing defining a chamber for receiving a container of medical waste. This chamber is connected to the antibacterial/antiviral filter to remove biological and chemical contaminants from the exhaust gas, also called out gas, of the container during heating. After the container of waste is placed into the chamber, a closure device seals the container into the chamber as a heat source brings the chamber to a temperature of preferably not less than 350° F. and preferably not greater than 385° F. to render the medical waste unreusable and sterile. A cooling device is located in the body portion to aid in the formation of a predetermined air and gas flow by directing discharges through the filter. This is accomplished by the creation of a negative pressure within the closure device and chamber where the container is placed. The negative pressure also assists the prevention of out flows of discharge from the body portion.

The present invention also provides for a method of heat processing the medical waste. This method includes the steps of accumulating the waste items into a container, closing the lid, and then heating the container to a temperature of preferably not less than 350° F. and preferably not more than 385° F. during which the lid of the container is sealed to the base of the container. The exhaust gas from the heating step is then filtered with an antibacterial/antiviral filter. The method further includes providing a reservoir as an additional volume of space to account for the inconsistent and sudden gas discharges which occur upon heating undetermined waste compositions. Furthermore, the method can provide for flowing essentially all out gas from heating the container into a predetermined path by the formation of a negative air pressure within the chamber holding the container and closure device.

Further objects and advantages of the present invention herein disclosed will become apparent to those skilled in the respective arts. However, all such modifications are deemed to be within the scope of the present invention as defined within the appended claims.

DETAILED DESCRIPTION

The present invention provides an apparatus and method for heat treating medical waste which overcomes the deficiencies of prior art and includes several new advantages. The present invention is an on-site medical waste processing system which is capable of processing all types of infectious medical waste, except human and animal body parts, radioactive waste and chemotherapeutic waste (depending on state regulations). In general, medical waste is comprised of different types of components such as plastic, cotton, aluminum, glass, etc. The present invention heats infectious medical wastes to a predetermined temperature of preferably not less than 350° F. and preferably not more than 385° F. to melt all the plastic portions of the waste. In the case of sharps material (needles, syringes, sutures, and IV tubing), the present invention renders the sharps material unrecognizable or unreusable, thereby allowing it to be disposed of as ordinary garbage. For soft or "red bag" wastes, such as gauze, cotton balls, gowns, etc., the exposure of this type of waste to the disclosed amount of heat renders the waste sterile and therefore allows it to be disposed of with ordinary garbage.

The present invention provides the advantage of a single on-site system to handle the sterilization or destruction of all types of regulated medical waste. This is accomplished by assuring that essentially all out gas from the heated waste container flows in a predetermined path. Additionally, a filter, preferably an anti-viral/anti-bacterial/charcoal filter, is placed in between the processing container and the exhaust. Discharges are directed through the filter by the creation of a negative air pressure within the closure device and the chamber where the waste container is placed to assure removal of essentially all airborne contaminants. The present invention further includes a method to handle unpredictable "burps" of gas which may occur when a waste load of undetermined composition is heated.

Figure 1:
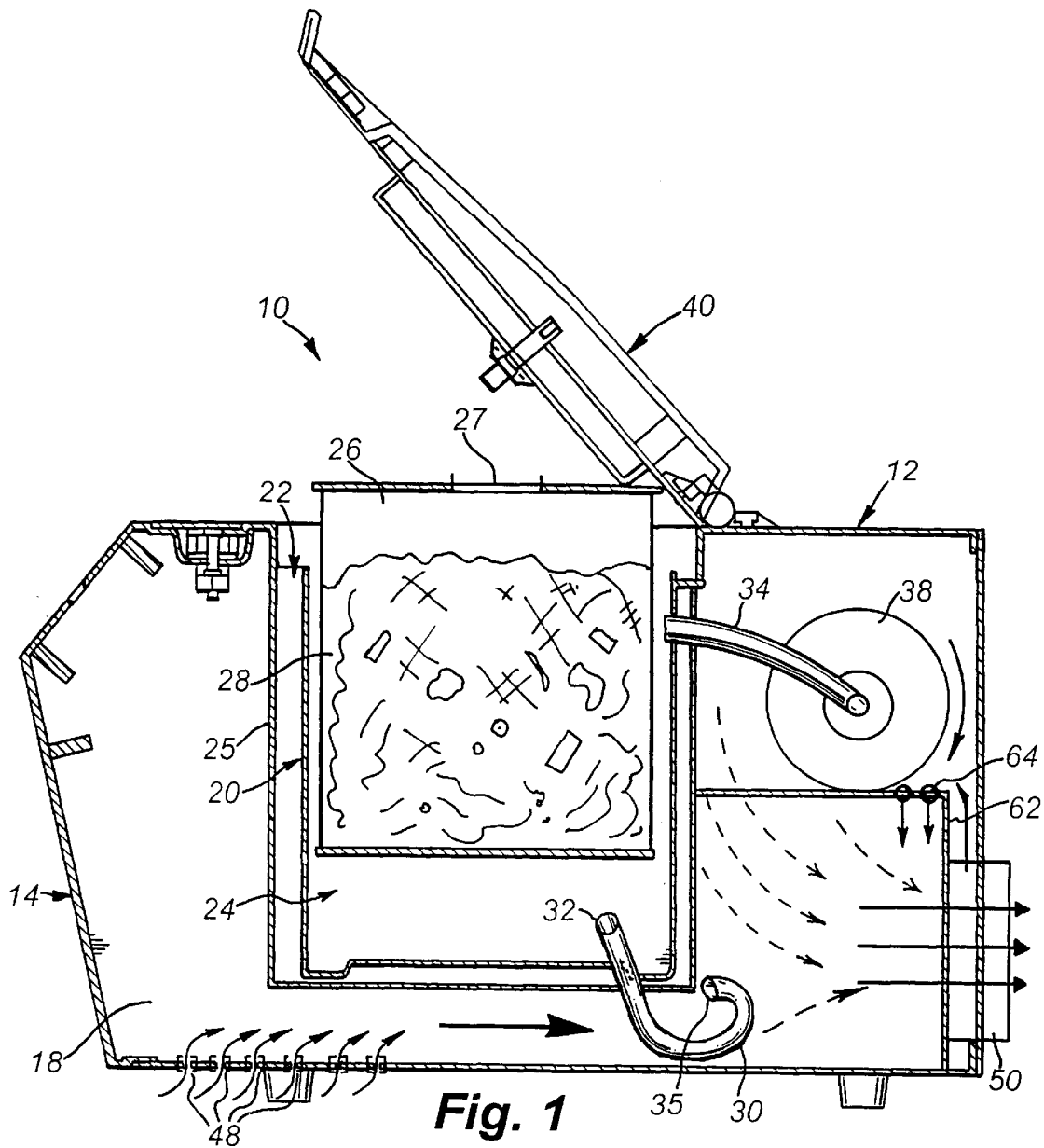
FIG. 1 is a schematic illustration of a side view of the present invention with a container of medical waste.
Figure 9:
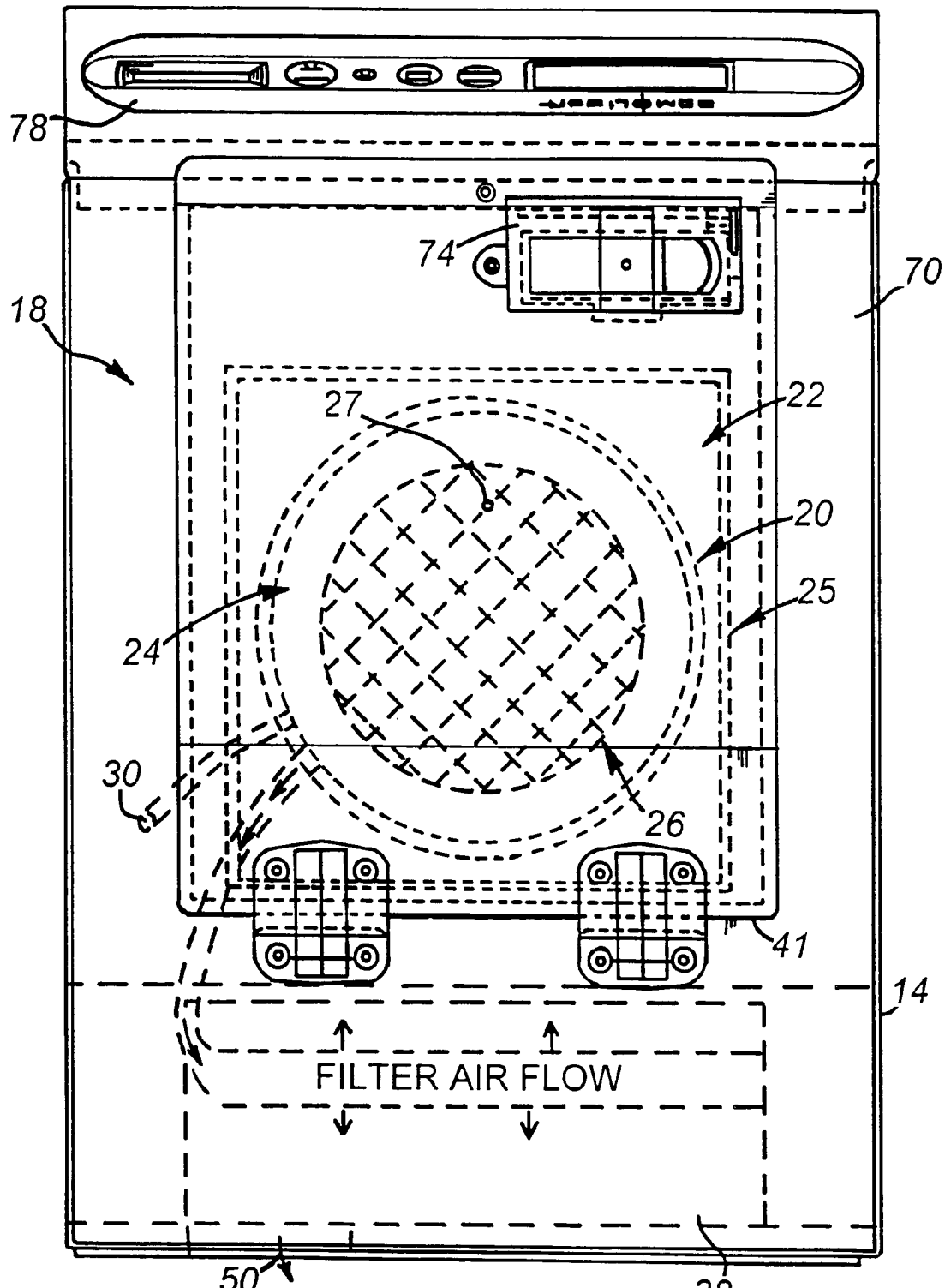
FIG. 9 is a schematic illustration of a top view of the present invention displaying the filter and filter air flow.

Referring to FIGS. 1 and 9, the apparatus 10 of the present invention is shown. FIGS. 1 and 9 show side and top views with a canister 26 being positioned in the apparatus 10. The present invention 10 includes a body portion 12 and a closure device 40. The body portion 12 includes an outer housing 14 and inner housing 20. An inner shell 25 is provided between the outer housing 14 and inner housing 20. The outer housing 14 and inner housing 20 cooperate to define a first chamber 18 within the body portion 12. The inner housing 20 and inner shell 25 cooperate to define a second chamber 22. Furthermore, the inner housing 20 defines a third chamber 24 within the body portion 12 of the present invention 10. This third chamber 24 is adapted to receive a container 26 which is filled with waste material 28, such as the types of medical waste described above. In FIG. 1, the closure device 40 is shown in the open position as a canister 26 is being placed into the third chamber 24 so that the canister 26 can be sterilized and the medical waste rendered unrecognizable.

FIG. 1 also discloses the features of a reservoir 30, which may be a tube, and a filter 38. The reservoir 30 extends through the inner housing 20 and opening 32 and into the first chamber 18. The reservoir 30 acts to provide a safety volume of space for gas from the container 26 and third chamber 24 which occurs upon heating the waste 28. Preferably, the reservoir 30 is in the form of a tube. This tube is referred to as a burp tube since it removes the unexpected burps of gas which occur during heating. The burp tube 30 can be made of any metal, silicone rubber, or Teflon® material. The tube 30 has an open end 35 within the first chamber 18 to introduce ambient air to purge the third chamber 24. Other alternative devices can be used as the reservoir, such as expandable bags.

The filter 38 is connected to the third chamber 24 through the inner housing 20 by means of a tube 34, channel, or other transport and connection device. The filter 38 is preferably an antibiological material filter, such as those which are capable of filtering viral and bacterial material. An example of a suitable filter is the FILTREAT® & type anti-viral/anti-bacterial filter produced by 3M of Minneapolis-St. Paul, Minn. A charcoal material is the preferred filtration material to be used with the filter 38. A dual stage, anti-viral/anti-bacterial-charcoal filter has the ability to entrap an airborne virus or bacteria, such as those present in the fumes from the heated medical waste. The filter 38 processes exhaust gas from the third chamber 24 as the container 26 is heated.

The present invention 10 also includes an exhaust system and air flow device 50 which acts in cooperation with the filter 38 and reservoir 30. The air flow device/exhaust system 50 ensure that air flow through the first chamber 18 is in a predetermined direction. The air flow device/exhaust system 50 brings in outside air through a plurality of openings 48 on the base of the body portion 12 of the present invention 10. This air flow system 50 creates a negative air pressure within the volume of space between the waste container 26 and inner housing 20, i.e., the third chamber 24, when lid 40 is closed. In this manner, the system 50 prevents the discharge of hazardous fumes or infectious microbials from the apparatus 10 as the waste material 28 is heated and sterilized. The air flow system 50 also operates to cool the outer housing wall 16 and the filter 38.

The body portion 12 of the present invention 10 is formed of any rigid material capable of withstanding the sterilization heat range and cycles, such as stainless steel sheet metal or plastics. The body 12 has dimensions of 19 inches deep by 13 inches wide, by 12¼ inches high in a preferred embodiment, but other sized machines can be produced.

Figure 2:
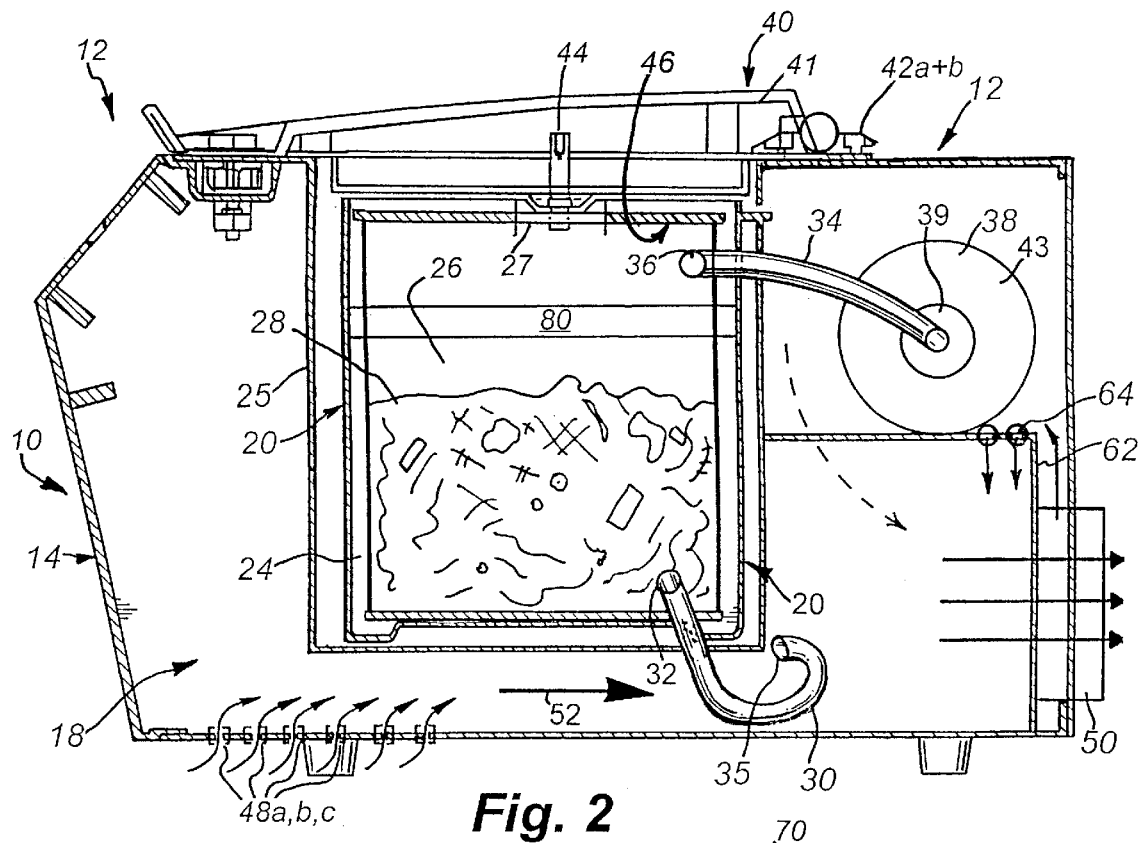
FIG. 2 is a schematic illustration of a side view of the present invention with the closure device in the closed position.
Figure 3:
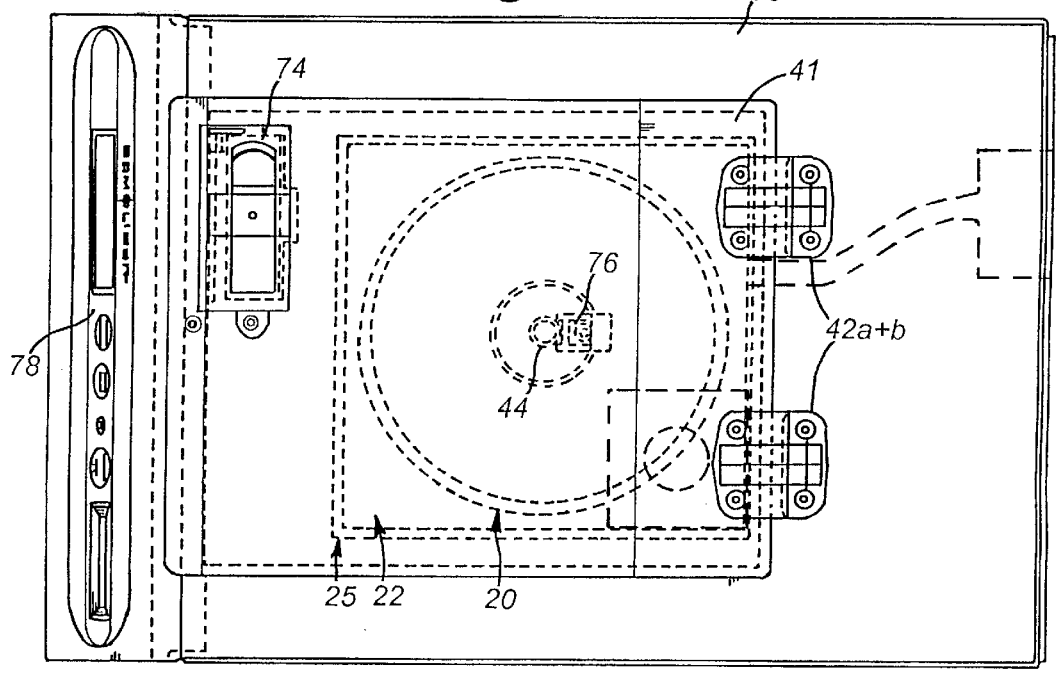
FIG. 3 is a schematic illustration of the top view of the present invention with the closure device in place.

Referring to FIGS. 2 and 3, the present invention 10 can be seen with closure device 40 closed, such as is the case of the apparatus in operation. The container 26 with the medical waste 28 is shown placed into the third chamber, preferably cylindrical in shape although other shapes are possible. The container 26 is a modified metal can having a special cap 46 with a vent hole 27 sealed on site after filling the can 26 with waste 28. Preferably, the container has a one gallon capacity approximately 6½ inches wide, 8 inches tall, with a waste collection opening of 2¼ inches in diameter and a pin sized vent hole 27 on the cap 46, but other sizes may be utilized. The closure device 40 has been brought into its closed position from its initial open position of FIG. 1. The closure device 40 may comprise a lid 41 attached to the top surface 70 of the outer housing 14 by mounting devices 42a and 42b. These mounting devices 42a and 42b are preferably pivotal or spring-like in nature to allow the lid 41 to be moved from a first open position to a second closed position. Other mounting devices 42 are within the scope of this invention, however, such as sliding devices, caps, screw on lids and other known devices in the art. Along with the mounting devices 42a and 42b, there may be an additional mounting or locking device 74 to ensure the lid 41 remains in a closed position.

Cap detection device 44 is provided to assure the presence of the cap 46 on the container 26. The cap detection device will prevent the machine from operating if a cap 46 is not detected on the canister 26. The cap detection device 44 includes a microswitch 76 with an arm. Microswitch 76 is electrically connected by conventional circuitry known in the art with an "on" position and an "off" position. When the closure device 40 is brought into the closed position, the cap detection device 44 will fall to a downward position and contact the cap 46 on the canister 26. Upon contact with the cap 46, the cap detection device 44 stops its downward travel and trips the microswitch 76. If no cap 46 is found on the container 26, then the cap detection device continues to travel downward. This will prevent operation of the apparatus 10 since the microswitch and arm will not be tripped to an "on" position.

A heat source 80 brings the medical waste to the desired temperature during operation and may be located in the third chamber 24. The heat source 80 can comprise a heater band which may extend around the periphery of the inner housing 20. Any heat transferable material can be used for the heater band. The band may be secured to the inner housing 20 preferably by self-adhesive backing or a ring clamp. In a preferred embodiment, the heat source 80 is an electric band heater with a preferred power of 700–1000 watts. This heat source 80 may also be located within the body portion 12 anywhere near the periphery of the inner housing 20. For example, a heat plate may be located at the base of the third chamber 24. In addition to electric heating, any standard heat source can be used which is known in the art.

In this manner, medical waste is accumulated in a container 26 which is then closed on site. The container 26 is placed into the third chamber 24 of the present invention 10 when the closure device 40 is in the open position. The third chamber 24 is slightly larger than the can with dimensions of approximately 7 inches, and therefore, an area of open space exists between the can 26 and the inner housing 20. Preferably, this space is less than one half inch. Once the container 26 is in position, the lid 41 is brought to the closed position with the cap detector device 44, mounting devices 42, and locking device 74 all properly positioned to ensure the canister 26 with the medical waste 28 is sealed in place in the third chamber 24. As the heat source 80 is brought to the proper temperatures for sterilization and/or to render the waste material unrecognizable and unreusable, the user of the device can monitor the container 26 through the display and control panels 78 shown on FIG. 3. The container 26 and the waste items 28 are heated to a temperature of preferably not less than 350° F. and preferably not more than 385° F. to ensure that the waste is rendered unrecognizable or sterile.

A typical process cycle time for a can of waste is approximately two and one half hours. The apparatus takes approximately 20 minutes to heat from room temperature to 350° F. after the container 26 is placed in the system. After reaching the desired temperature, the waste is held and heated at this temperature for a minimum of 90 minutes. The lid 41 is maintained in the closed and locked position until a safe operating temperature is reached. The container 26 is then allowed to cool to a safe handling temperature of approximately 115° F. before the container 26 can be removed. This cool down takes about 40 minutes.

Figure 4:
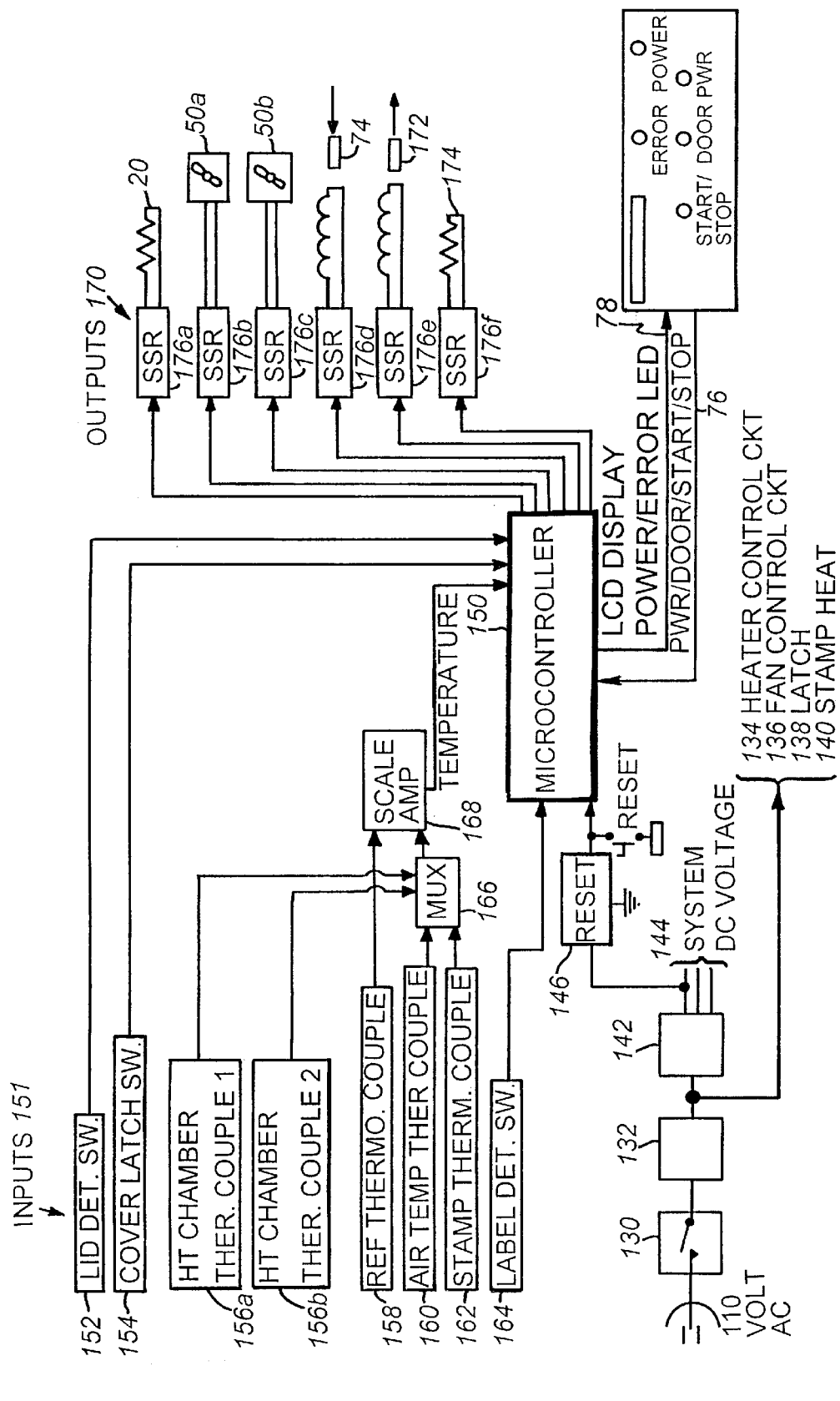
FIG. 4 is a schematic illustration of the electrical connections of the present invention in a preferred embodiment.

Referring to FIG. 4, the basic electrical connections of a preferred embodiment of the present invention can be seen. The system receives 110 volt AC from an outside source which is electrically connected to a power switch 130. From the power switch 130, the electrical connection is made with a line filter 132 and the power supply 142. The line filter 132 distributes the current to four individual circuits. These circuits comprise the heater control circuit 134, the air flow device circuit 136, the latch circuit with a lid 138, and a stamp heater circuit 140. The stamp heater (not shown) generates a label for the container which indicates that the waste in the container 26 has been rendered sterile and unreusable. The label is only generated when a heat cycle is successfully completed.

From the line filter 132, the electrical connection is made with the power supply 142 and the direct current voltages of the system 144. The system reset switch 146 is electrically connected to the system voltages 144 and the reset switch feeds into the microcontroller 150. The microcontroller 150 receives a series of inputs 151 which electrically connect through the microcontroller 150 to a series of outputs 170. Further, microcontroller 150 is electrically connected to the micro switch 76 which acts as a safety device in conjunction with the cap detection device 44 and thereby controls power to the apparatus. The LCD display panel 78 is also in electrical communication with the microcontroller 150.

The series of inputs 151, which are in electrical communication through the microcontroller 150 with the outputs 170 can be summarized as follows. Lid detection switch 152, the cover latch switch 154 and label detection switch 164 are all directly in electrical contact with the microcontroller 150. As can be surmised, each of these switches is named for the respective part to the apparatus which it controls. A series of thermalcouples are also provided as inputs 151 to the microcontroller 150. A pair of thermalcouples 156a and 156b are provided for the inner housing member 20. These thermalcouples 156a and 156b are sequentially and electrically connected by multiple circuit (MUX) 166, to a scale amplifier 168 and into the microcontroller 150. A reference thermal couple 158 is provided in electrical connection with the scale amplifier 168 to compensate the amplifier 168 for the ambient temperature. Further, an air temperature thermal couple 160 and a stamp thermalcouple 162 are in electrical connection with MUX 166 which is electrically connected to the scale amplifier and microcontroller as well.

The outputs 170 include electrical connections through solid state relays 176a-176f to the inner housing 20, to each of the exhaust fans 50a and 50b, to the lid latch 74, to the stamp solenoid 172, and to the stamp heater 174 for the label dispenser (not shown).

Referring back to FIG. 3, it should be noted that the waste 28 in the canister 26 will often include an amount of thermoplastic material from items such as syringes. This material will melt during the heating step of the process. Upon hardening, this melted thermoplastic material becomes a biologically sterile and unitary mass in which the sharp edges and points of syringes, tubes and needles are at least partially encapsulated within the resin. The waste 28 is therefore, rendered unrecognizable and/or unreusable, and sterile due to the heating and hardening process. This hardened mass should preferably be larger than the collection opening on the container 26 which is smaller than the width of overall container 26 to assist in the prevention of the removal of the mass from the container 26 in cooperation with the container cap 46.

The waste 28 can also include nonthermoplastic materials and soft or "red bag" wastes. The heat renders this type of waste sterile, thereby allowing it to be disposed of with ordinary trash.

In order to appreciate the advantages and functions of the burp tube 30, it should be understood that when medical waste, or any waste for that matter, which is comprised of different materials is heated, there is no orderly heating of the material. The waste material does not undergo an even or uniform heating, as there are different compositions and localized volumes within the container 26. Due to this random heating, the present invention 10 is designed to handle the associated unpredictable heating and gas expansion problems which may occur, such as alcohol vaporization which will be more thoroughly described below.

The canister 26 has a vent hole 27 which allows gas to flow out of the canister during heating. This gas initially flows toward the filter 38 because of the predetermined air flow and then fills up the space in the third chamber 24 immediately surrounding the container 26. As this third chamber 24 is filled, gas enters the burp tube 30. This tube 30 provides an additional safety volume of space for gas which vents from the container 26. Tube 30 gives the system 10 the ability to handle the inconsistent heating of a given medical waste load. The different thermal conductivity rates, different out gases, and random reactions from the associated random waste materials and uneven heating will occasionally cause an unpredictable burp of gas to be released from the container 26. The burp tube 30 has sufficient capacity within the tube to handle this inconsistency of gas flow and provides a safety volume of space into which the vented gas can expand. In a preferred embodiment, the burp tube 30 is approximately 8 inches long with an inner diameter of ⅛" and outer diameter of ¼".

As an alternative to the tube, the opening 32 can be connected to a reservoir or other additional gas storage area where the extra gas can be stored until the system is capable of discharging. The reservoir or tube provides the advantage of eliminating the need for a larger third chamber 24 which may be necessary to handle discharge volume inconsistencies. Therefore, less heat is required to heat the air space which surrounds the container 26 in the third chamber 24.

Thus, in operation, as the container 26 is heated, the waste material 28 heats unevenly. Within the waste material 28, there will be pockets of materials with different densities which heat at different times and at different rates. For example, if a pocket of alcohol is heated within the medical waste 28, it will start to out gas before the surrounding materials because of the low vapor point of the alcohol. This will produce a rapid and voluminous flow of gas which would cause the gas and the hazardous fumes and infectious microbials to either escape from the top of the third chamber 24 or pass through the filter 38 too quickly to be dissipated or trapped. In order to accommodate this sudden increase of gas flow from the container 26, the burp tube 30 is provided.

In a preferred embodiment of the present invention 10, the filter 38 is a dual stage charcoal type filter. The gas enters the anti-bacterial/antiviral microbial and biological portion 39 of the filter 38 first and then passes through the charcoal portion 43 of the filter 38. In order for a charcoal type filter to be an effective filtration material, whatever needs to be filtered should pass over and around the charcoal slowly enough for the charcoal to trap and absorb the odors. Alcohol, a material commonly found in medical waste, has a low vapor point. As alcohol is gasified in operation of the present invention, it will condense quickly on the filter if the filter is cool. The temperature of the filter, therefore, should be maintained at a point higher than the condensation point of alcohol in order to prevent such condensation on the filter. Alcohol and charcoal have a natural affinity which causes the recondensed alcohol to surround the charcoal and prevent absorption of odors by the charcoal. To maintain the filter temperatures and prevent alcohol condensation, some of the heat generated from the third chamber 24 is allowed to radiate back to the filter 38. This is accomplished by allowing radiant heat from the third chamber 24 to escape through the shell 25 to heat the filter cartridge 38 and also by restricting the flow of cooling air around the filter 38. The inner shell 25 encloses the third chamber 24 on all sides in a preferred embodiment. The inner shell 25 can act as a baffle, provide a location for anchoring items, and define a pathway in which air may be blown in order to cool third chamber 24. Various insulation materials can be mounted on the inner shell 25 and within the apparatus, with a 12 inch ceramic blanket of Insulwool, commercially available from ceramic supply houses, being preferred. The insulation keeps the apparatus at an acceptable temperature for operation.

In any waste load, virus or bacteria may be present which could become airborne prior to the waste load reaching a "kill" temperature. The use and location of an anti-viral/anti-bacterial material eliminates therefore, this possibility by trapping all airborne viruses and bacteria. As the temperature reaches the "kill" zone, the apparatus can sterilize the filter 38 with each cycle.

The exhaust gas passes in a predetermined and controlled direction through the exhaust system/air flow device 50 which maintains hazardous fumes and infectious microbials within the third chamber 24, tube 34, and filter 38. In this manner, it is assured that the filter 38 can trap the airborne virus and/or bacteria as the air flow within the present invention requires biological materials to pass through the filter 38 before reaching the exhaust system/air flow device 50.

Figure 5:
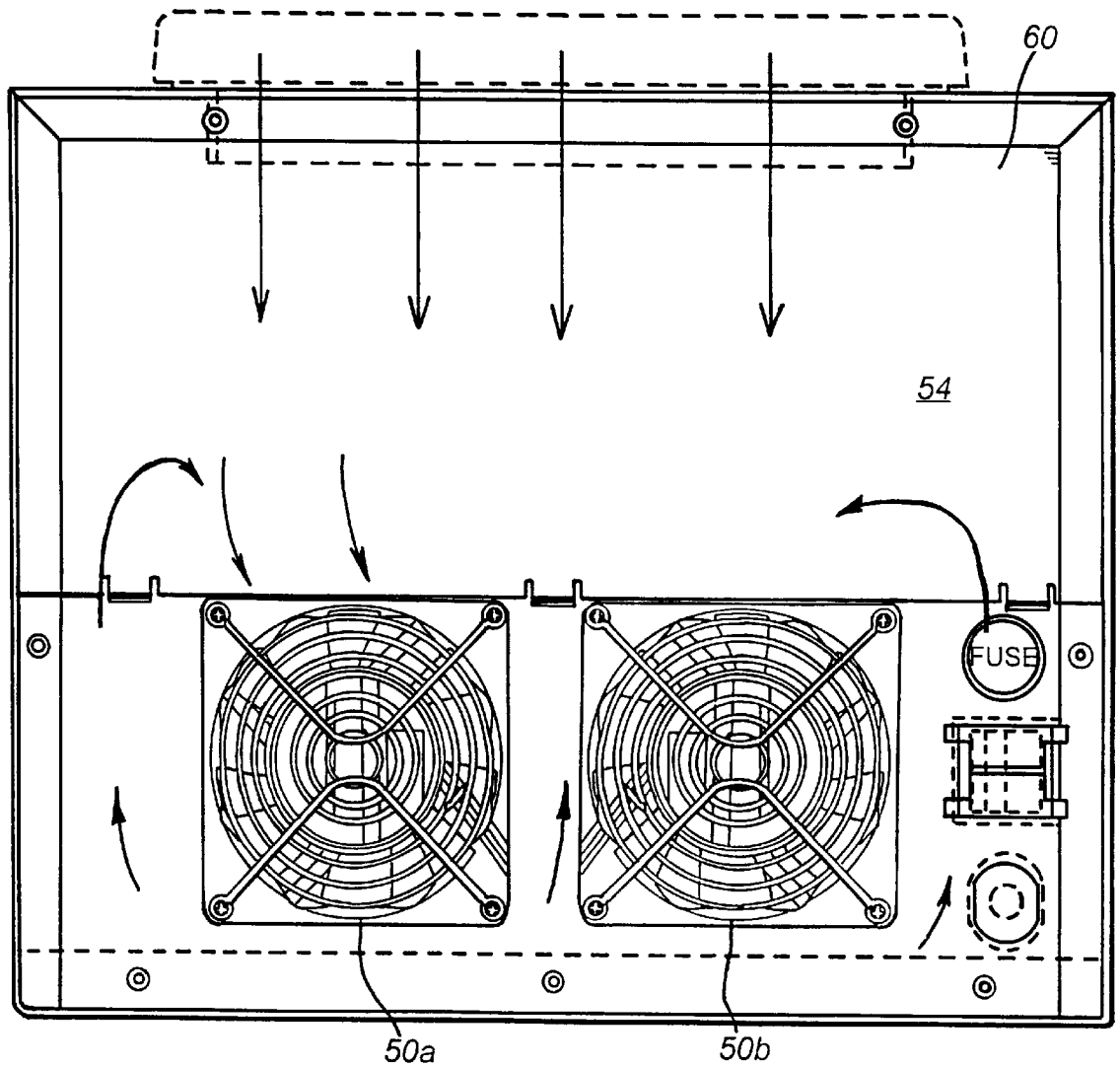
FIG. 5 is a schematic illustration showing the negative air pressure created by the cooling device of the present invention.
Figure 6:
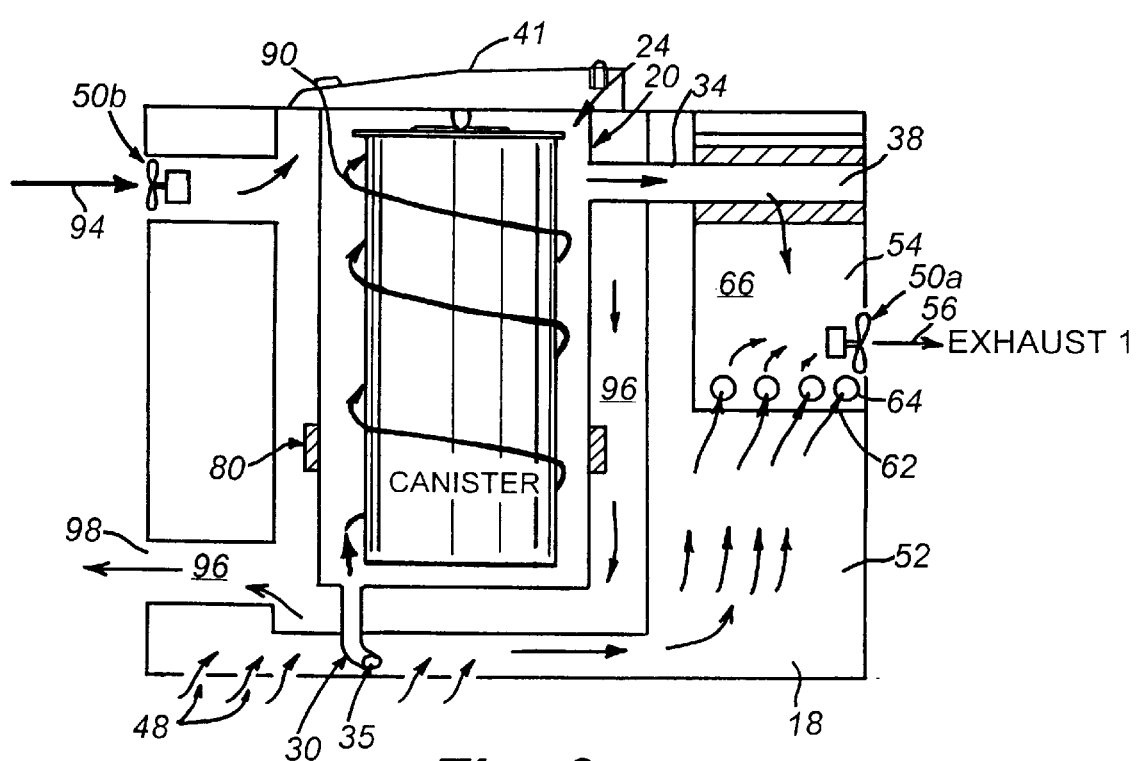
FIG. 6 is a conceptual illustration of the air flow through the apparatus of the present invention from a side view.

Referring to FIGS. 2, 5, and 6, the features of the exhaust system/air flow device 50 can be more readily seen. Referring first to FIG. 5, the air flow device 50 is disclosed in a preferred embodiment as a pair of fans, 50a and 50b, located on the back 60 of the apparatus 10. The first fan 50a cools the outer housing 14 and also provides the negative air pressure which ensures the air and gas flow through the filter 38. The first fan 50a is in continuous operation during use of the apparatus 10. This fan preferably has a capacity of 0.075 inches of water and is operated at a 15–25 c.f.m. rate. This creates an air flow which is sufficiently slow to allow the filter to operate effectively. Much greater flow rates would prevent the charcoal/filter from being fully effective because contaminants would not remain in the filter for sufficient time to be absorbed. Therefore, the longer the latency time of the contaminants in the filter 38, the greater the filter efficiency and ability to process the contaminants. The second fan 50b intakes outside air and cools the third chamber 24 after a heating cycle. This fan preferably is operated at a rate of 25–35 c.f.m. The fans are commercially available from numerous manufacturers.

There are three distinct controlled air flows in the present invention as shown in the conceptual illustration of FIG. 6. The first air flow 52 comprises the majority of the air passing through the system. The first fan 50a draws in air from outside of the apparatus 10 through the plurality of pressure control ventilating openings 48 located on the base of the body portion 12. This first chamber controlled air flow 52 is drawn through the openings 48 into the first chamber 18 towards the air flow device 50. Similarly, the air flow device 50a creates negative air pressure at the top of the container 26 and apparatus 10, which passes through the filter 38. This negative air pressure 54 joins with the first chamber controlled air flow 52 and passes through the exhaust and air flow device 50 at point 56. This predetermined and first chamber controlled air flow 52 ensures that the working environment which surrounds the apparatus 10 remains essentially free of microbials and hazardous fumes which may be discharged from the container 26 during heating.

During the actual processing of the waste 28 and independent of the cooling function, the first chamber controlled air flow 52 serves multiple functions. The first chamber controlled air flow 52 is generated by the fan 50a located in a plenum 62 which is an integral part of the system. The plenum 62 is a frame which separates the filter 38 and encases the fan 50 away from the first chamber 18. The air flow through the plenum 62 is provided from two sources. The majority of the air flow is the first chamber control air 52 which passes through a series of relatively large pressure control ventilating holes 64 in the periphery of the plenum 62 and near the fan intake. A high volume for this first chamber controlled air 52 is most preferably mixed with gasses through the charcoal filter 38 to prevent an unsafe condition of high alcohol concentration. The remainder of the air through the plenum 62 is typically a very small fraction and derived from purge air flow discussed below.

A secondary function of the first chamber controlled air flow 52 is to maintain outer housing 14 at an acceptable temperature. Further, the filtered canister 38 is held within the air flow plenum 62 in close proximity of the inner housing 20. Some of the process heat is radiated into the plenum cavity 66 to thereby elevate the temperature of the canister. This reevaporates any early process condensation and prevents condensation on the filter 38 in later stages of the process.

The second air flow 90 of the present invention is the purge air. This is defined as the air which passes through the inside of the third chamber 24 and then through both stages of the filter 38. This purge air 90 passes through a large exhaust tube at the top of the apparatus and through the large volume charcoal filter canister 38 and into the main airstream within the plenum 62 before passing with exhaust 56.

The purge air intake location 35, i.e., the reservoir opening, allows the purge air 90 to sweep the volume of space within the third chamber 24, between the canister 26 and the inner housing 20 from the bottom to the top to ensure that an envelope of clean air surrounds container 26. This envelope of clean purge air 90 which surrounds the container 26 in conjunction with the reservoir 30 provides the additional function of a ballast which absorbs the out gassing pressure spikes created by random bursts of boiling material. The purge air 90 acts as a vehicle to carry the outgassing products from the top of the container to the filter 38. The purge air 90 sweeping action also ensures that at the end of heat processing the medical waste, no residual odor will remain in the apparatus 10.

Although the volume of purge air 90 is very small, it is much greater than the volume of the out gassing products. This enables the out gassing to reach the filter and prevent the build up of the extremely odiforous out gasses above the container 26. Therefore, the high volatility of certain items of medical waste, such as alcohol, which may be initially driven off and partially condensed in the filter canister 38, can be reevaporated by the combination of the heated filter canister 38 and the flow of the heated purge air 90 which has passed through the apparatus 10. It is this same high ratio of clean air to filtered vapors which helps to maintain a low odor level.

Figure 7:
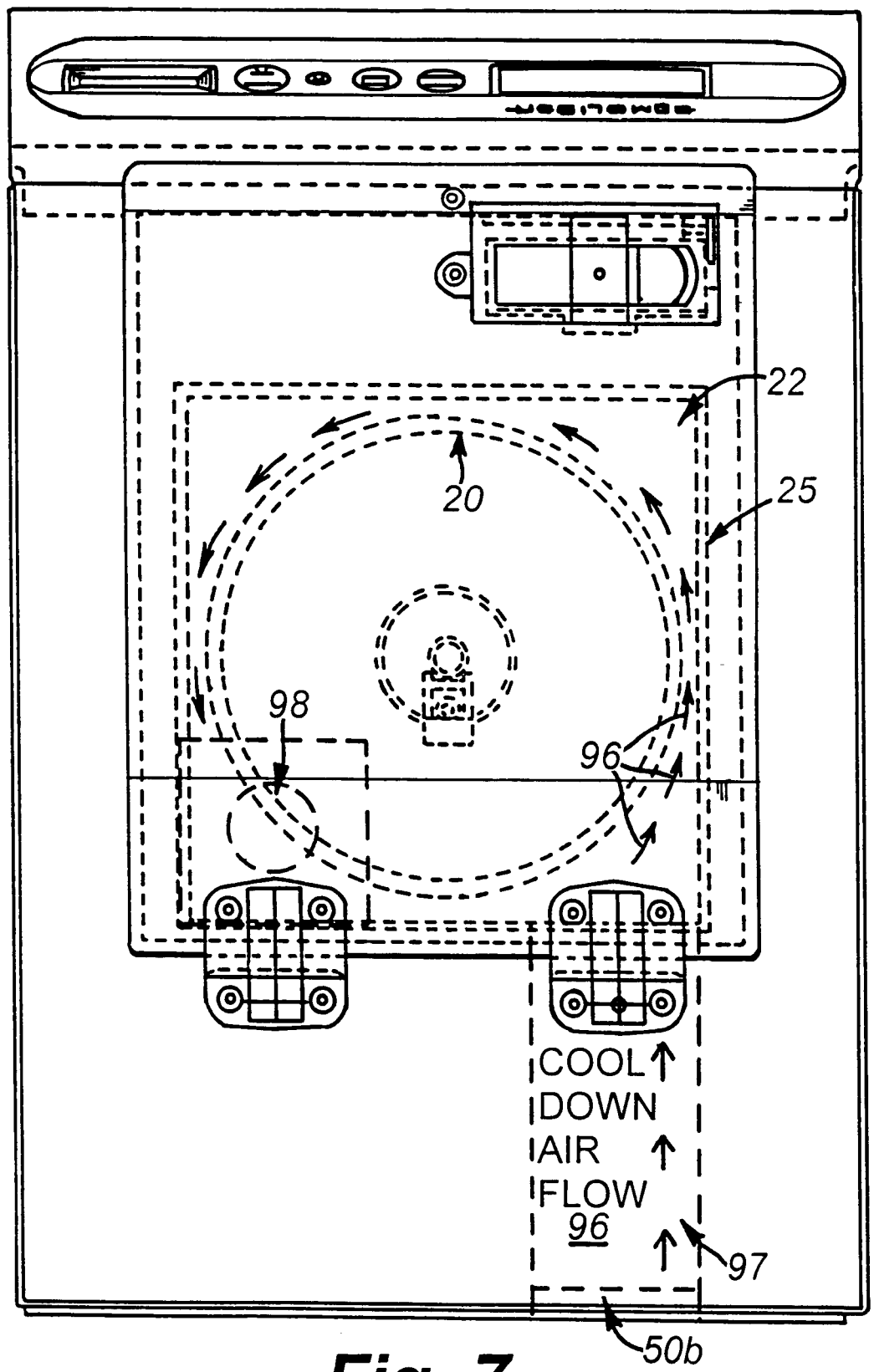
FIG. 7 is a schematic illustration of the top view of the present illustration and the cool down air flow through the apparatus.
Figure 8:
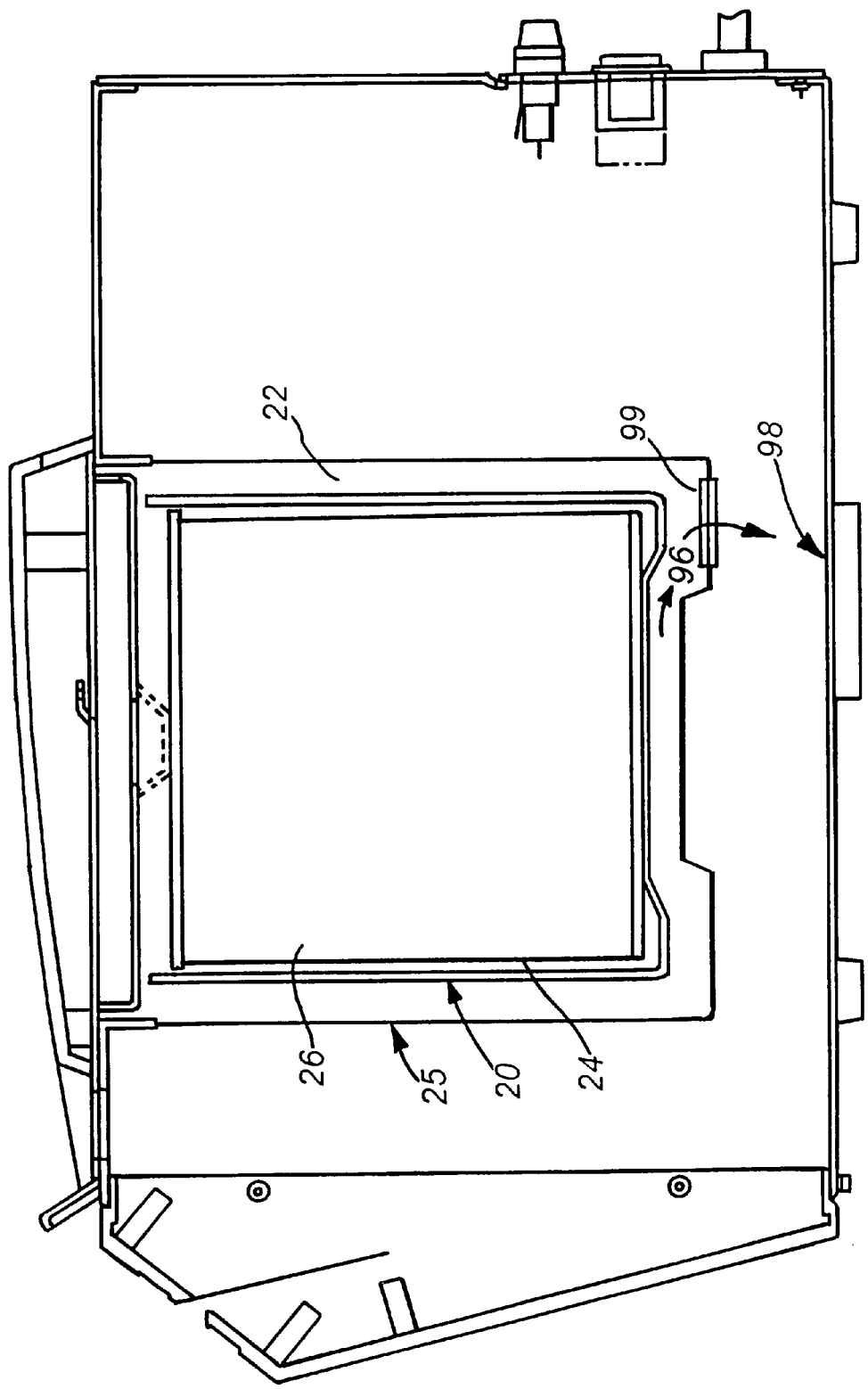
FIG. 8 is a schematic illustration of a side view of the present invention and the cool down air flow.

The third air flow of the present invention is the cool down air flow 96 as seen in FIGS. 6, 7, and 8. This air flow 96 is created by the second fan 50b bringing in outside air 94 through tube 97 and into second chamber 22. The cool down air flow 96 cools the second chamber 22, inner housing 20, and inner shell 25 after a heating cycle and exits the apparatus as exhaust at air flow exit 98 after passing through an opening 99 at the base of inner shell 25.

Having thus described at least one illustrative embodiment of the invention, various alterations, modifications, and improvements will readily occur to those skilled in the art. Such alterations, modifications, and improvements are intended to be within the spirit and scope of the invention. Accordingly, the foregoing description is by way of example only and is not intended as limiting.

What is claimed is:

1. A process for heat-processing medical waste in an apparatus having a chamber, comprising the steps of:

heating a container of waste in the chamber using a conductive heater thermally coupled to the chamber, thereby rendering the waste biologically safe;

directing discharge gases from said container in a predetermined direction;

filtering said discharge gases with a filtration device;

directing ambient air from outside the apparatus into the chamber during the step of heating; and mixing the discharge gases with the ambient air.

2. The process of claim 1 wherein said filtration device is a dual stage filter.

3. The process of claim 2 wherein said dual stage filter comprises a first component having an antibacterial/antiviral material and a second component having an odor-trapping material.

4. The process of claim 1 further comprising the step of providing a reservoir for discharges from said container.

5. The process of claim 1 wherein said discharge gases are directed in the predetermined direction toward said filtration device by an air flow device.

6. The process of claim 5 wherein said air flow device creates a negative pressure over said container.

7. The process of claim 1 wherein said waste includes an amount of thermoplastic material which melts upon said heating step.

8. The process of claim 7 further comprising the step of hardening said melted thermoplastic material to create a biologically sterile unitary mass in which sharp edges and points are at least partially encapsulated.

9. The process of claim 8 wherein said container of waste has an opening, and said unitary mass is larger than said opening of said container.

10. A process for heat-processing medical waste, comprising the steps of:

providing a chamber to receive a container of waste, said chamber being larger than said container so that a volume of space exists in said chamber after receipt of said container by said chamber;

heating said container of waste thereby rendering the waste biologically safe, wherein the heating is accomplished using a conductive heater thermally coupled to the chamber;

directing discharge gases from said container in a predetermined direction by an air flow device;

filtering said discharge gases with a filtration device;

providing a purge air flow of ambient air through said volume of space in said chamber during the step of heating to purge said volume of space and direct the discharge gases from said container to said filtration device; and mixing ambient air from outside the chamber with the discharge gases prior to discharging the discharge gases from the chamber.

11. The process of claim 10 wherein said filtration device is a dual stage filter.

12. The process of claim 11 wherein said dual stage filter comprises a first component having an antibacterial/antiviral material and a second component having an odor-trapping material.

13. The process of claim 10 wherein said air flow device creates a negative pressure over said container.

14. The process of claim 10 wherein said waste includes an amount of thermoplastic material which melts upon said heating step.

15. The process of claim 14 further comprising the step of hardening said melted thermoplastic material to create a biologically sterile unitary mass in which sharp edges and points are at least partially encapsulated.

16. The process of claim 15 wherein said container of waste has an opening, and said unitary mass is larger than said opening of said container.

17. An apparatus for thermal processing of medical waste, the apparatus comprising:

a body portion having a chamber to receive a container of medical waste;

a conductive heater contained within the body portion and thermally coupled to the chamber to provide heat to the container;

a filtration device contained within the body portion and having an inlet coupled to the chamber and having an outlet to provide filtered air;

a first air plenum, contained in the body portion, having an inlet to receive ambient air and an outlet to provide the ambient air received in the inlet to the chamber;

a second air plenum, contained in the body portion, having an inlet to receive ambient air and an outlet;

a first air flow device constructed and arranged to draw air through a first path and a second path, mix air drawn from the first path with air drawn from the second path to create mixed air, and exhaust the mixed air drawn from the body portion;

wherein the first path includes the first air plenum, the chamber and the filtration device, and the second path includes the second air plenum; and wherein the apparatus is constructed and arranged to draw ambient air through the first air plenum and into the chamber while the conductive heater is heating the container.

18. The apparatus of claim 17, wherein the body portion further includes a second air flow device and a third air plenum having an inlet and an outlet, wherein the second air flow device is constructed and arranged to draw ambient air through the third air plenum to cool the container after the medical waste has been processed.

19. The process of claim 1, wherein the container has a top with holes to release discharge gases during the heating step, and wherein the step of discharging includes a step of directing ambient air from outside the apparatus through an air flow path across the top of the container during the step of heating.

20. The process of claim 19, further comprising a step of directing ambient air through an air plenum around the chamber to cool the chamber and the container after the step of heating is finished.

21. The process of claim 10, further comprising a step of directing ambient air through an air plenum around the chamber to cool the chamber and the container after the step of heating is finished.

22. The process of claim 1, wherein the step of heating includes a step of heating the container of waste to a temperature of not less than 350° F. and not more than 385° F.

23. The process of claim 10, wherein the step of heating includes a step of heating the container of waste to a temperature of not less than 350° F. and not more than 385° F.

24. The apparatus of claim 17 wherein said filtration device includes a dual stage filter.

25. The apparatus of claim 24 wherein said dual stage filter comprises a first component having an antibacterial/antiviral material and a second component having an odor-trapping material.

26. The apparatus of claim 17 wherein said air flow device is constructed and arranged to create a negative air pressure over said container to direct discharges from the container during heating of the container through said filtration device.

* * * * *